(12) United States Patent
Shichida et al.

(10) Patent No.: US 7,560,012 B2
(45) Date of Patent: Jul. 14, 2009

(54) GAS SENSOR

(75) Inventors: Takafumi Shichida, Nagoya (JP);
Takaya Yoshikawa, Nagoya (JP);
Takashi Nakashima, Nagoya (JP);
Satoshi Ishikawa, Nagoya (JP)

(73) Assignee: NGK Spark Plug Co., Ltd., Aichi (JP)

( * ) Notice: Subject to any disclaimer, the term of this patent is extended or adjusted under 35 U.S.C. 154(b) by 806 days.

(21) Appl. No.: 10/525,816

(22) PCT Filed: Aug. 27, 2003

(86) PCT No.: PCT/JP03/10887

§ 371 (c)(1),
(2), (4) Date: Feb. 25, 2005

(87) PCT Pub. No.: WO2004/023130

PCT Pub. Date: Mar. 18, 2004

(65) Prior Publication Data

US 2005/0241937 A1 Nov. 3, 2005

(30) Foreign Application Priority Data

Aug. 27, 2002 (JP) ............................. 2002-247441

(51) Int. Cl.
*G01N 27/407* (2006.01)
*G01N 27/406* (2006.01)
*G01N 27/26* (2006.01)
(52) U.S. Cl. ..................... 204/428; 204/424; 204/431; 204/429; 205/775; 205/782; 205/783.5
(58) Field of Classification Search ................ 204/431, 204/424, 428, 429; 205/782, 783.5
See application file for complete search history.

(56) References Cited

U.S. PATENT DOCUMENTS 5,707,504 A 1/1998 Jyouno et al.

(Continued)

FOREIGN PATENT DOCUMENTS

JP 8-254521 A 10/1996

(Continued)

*Primary Examiner*—Alex Noguerola
*Assistant Examiner*—J. Christopher Ball
(74) *Attorney, Agent, or Firm*—Sughrue Mion, PLLC

(57) ABSTRACT

A gas sensor is constructed as follows. A protector (4) covering around a gas sensing element (2) has an inner hollow-cylindrical portion (6) and an outer hollow-cylindrical portion (7) that is provided coaxially with the inner hollow-cylindrical portion (6) with an air space (8) in between. Outer-wall gas inlet openings (13) are formed in the outer hollow-cylindrical portion (7), and guiding bodies (10) extending inward are attached to the outer-wall gas inlet openings (13). Inner-wall gas inlet openings (11) are formed in the inner hollow-cylindrical portion (6) at positions nearer to the gas sensing element (2) than the outer-wall gas inlet openings (13). A side wall (9) face of the inner hollow-cylindrical portion (6) opposite the outer-wall gas inlet openings (13) is formed so as to be parallel to a side wall (12) of the outer-hollow cylindrical portion (7) or so as to have a slop-like shape with a diameter enlarging in the axial direction toward a bottom wall (17) of the protector (4). A discharge opening (15) for a gas to be measured is formed in the bottom wall (17).

9 Claims, 11 Drawing Sheets

U.S. PATENT DOCUMENTS

| | | |
|---|---|---|
| 6,279,376 B1 | 8/2001 | Yamada et al. |
| 6,346,179 B1 | 2/2002 | Makino et al. |
| 6,726,819 B2 | 4/2004 | Atsumi et al. |

FOREIGN PATENT DOCUMENTS

| | | | |
|---|---|---|---|
| JP | H10-111265 | * | 4/1998 |
| JP | 2000-28571 | | 1/2000 |
| JP | 2000-171429 A | | 6/2000 |
| JP | 2000-171430 | | 6/2000 |
| JP | 2001-099807 | * | 4/2001 |
| JP | 2001-99807 A | | 4/2001 |
| JP | 2001-228112 | | 8/2001 |
| JP | 2001-343356 | * | 12/2001 |
| JP | 2001-343356 A | | 12/2001 |
| JP | 2002-236105 | * | 8/2002 |
| JP | 2002-236105 A | | 8/2002 |
| JP | 2003-75396 A | | 3/2003 |
| WO | WO 01/22073 A1 | | 3/2001 |

\* cited by examiner

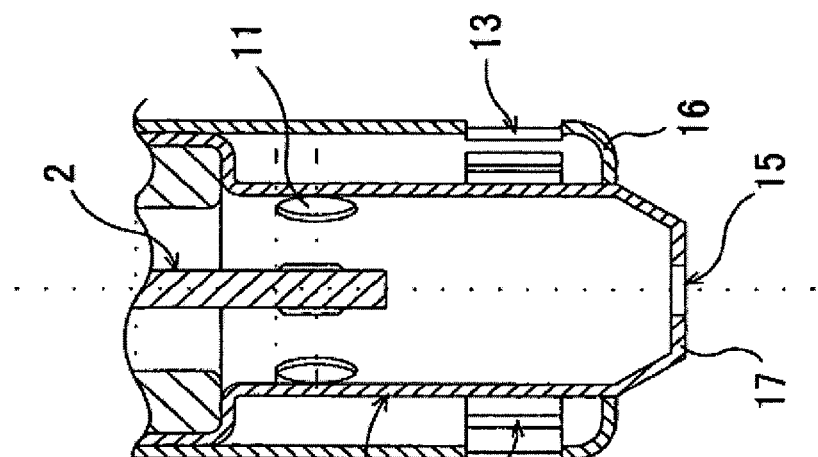
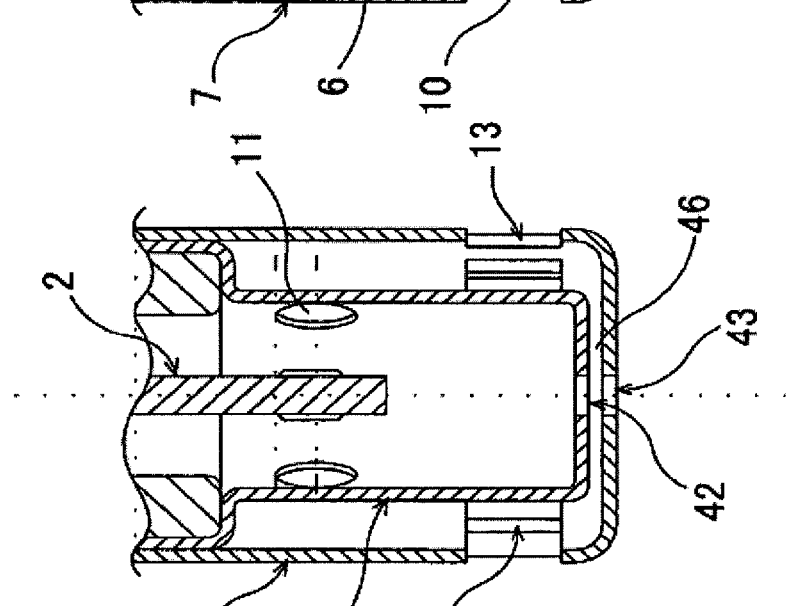
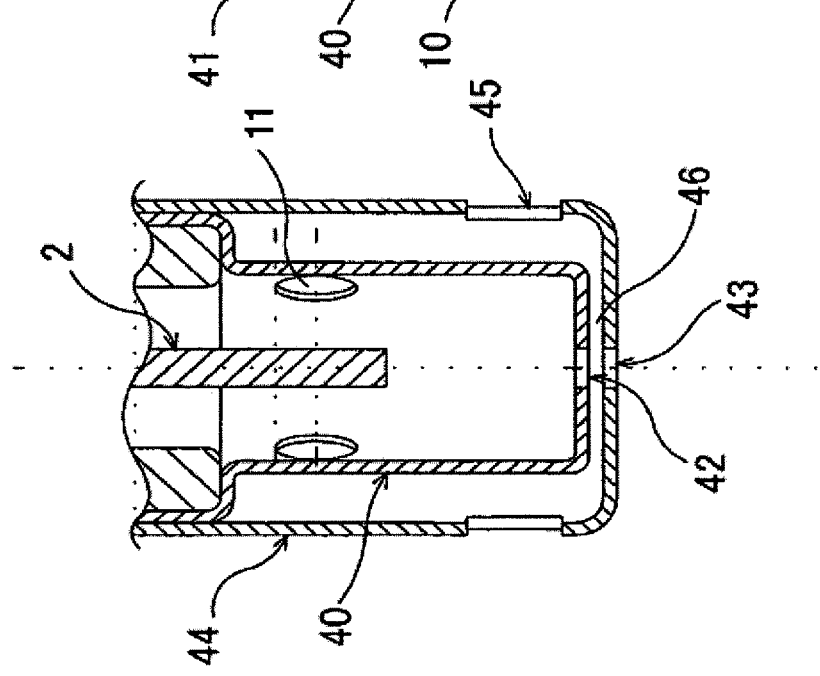

GAS SENSOR

TECHNICAL FIELD

This invention relates to a gas sensor, such as an oxygen sensor and a $NO_x$ sensor, which is used in a state exposed to a gas to be measured, and which comprises a protector that protects a gas sensing element accommodated therein from moisture contained in the gas to be measured.

BACKGROUND ART

Heretofore, gas sensors have been developed which are attached to an internal combustion, like an automobile engine, and detect specific gas components in exhaust gas (a gas to be measured). Among such gas sensors, a gas sensor (oxygen sensor), which detects oxygen concentration, and a $NO_x$ sensor, which detects nitric oxide gas concentration, are known to use a gas sensing element composed of a solid electrolyte such as zirconia.

Generally, the gas sensors of this type have a structure in which a gas contact part of the gas sensing element is exposed to the exhaust gas. The gas sensing element is heated to high temperatures (approximately 300° C.) by a heater to be activated, and detect the specific gas components in the exhaust gas.

The gas sensing element is made of ceramics and hence, sensitive to thermal shock. Therefore, if moisture in the exhaust gas is adhered to the gas sensing element which has been heated to high temperatures, a crack may be produced and cause damage to the gas sensing element.

For the above reason, a protector that covers the gas contact part of the gas sensing element is attached to the gas sensor so as to protect the gas sensing element from water droplets.

The protector is provided with inlet openings and outlet openings for the gas to be measured in its side wall or bottom wall. The gas to be measured is introduced from the inlet openings of the protector to the gas contact part of the gas sensing element and discharged from the outlet openings. The protector performs the introduction and discharging of the gas to be measured.

There is a gas sensor comprising a two-tiered protector composed of an inner hollow-cylindrical portion (a first hollow-cylindrical portion) and an outer hollow-cylindrical portion (a second hollow-cylindrical portion), in order to effectively remove moisture contained in the gas to be measured, and introduce and discharge the gas to be measured.

In this gas sensor, a side wall of the inner hollow-cylindrical portion and a side wall of the outer hollow-cylindrical portion are coaxially disposed with an air space therebetween. In these side walls, inlet openings of the gas to be measured (first gas inlet openings and second gas inlet openings) are formed. Also, at the inlet openings of the outer hollow-cylindrical portion, guiding bodies are disposed to produce a swirling flow that surrounds an outer face of the side wall of the inner hollow-cylindrical portion. Thereby, the gas to be measured introduced from the inlet openings of the outer hollow-cylindrical portion is divided into relatively heavier water droplets and relatively lighter gas components by a function of the guiding bodies for producing the swirling flow. The gas to be measured from which the moisture is removed is carried into the inner hollow-cylindrical portion from the inlet openings of the inner hollow-cylindrical portion, and brought into contact with the gas sensing element so that the specific gas components in the gas to be measured are detected. After this, the gas to be measured is passed through a discharge opening (a first side gas discharge opening) provided in the bottom wall of the inner hollow-cylindrical portion and discharged from a discharge opening (a second side gas discharge opening) provided in the bottom wall of the outer hollow-cylindrical portion (e.g., refer to a patent literature 1).

[Patent literature 1]
Unexamined Japanese Patent Publication No. 2001-099807 (pages 4 to 7, FIGS. 1 to 5)

DISCLOSURE OF THE INVENTION

However, in a gas sensor disclosed in the Unexamined Japanese Patent Publication No. 2001-099807, a gas discharge opening formed in an inner hollow-cylindrical portion is provided inside an outer hollow-cylindrical portion. Therefore, replacement of the gas to be measured inside the protector is insufficient. There is a problem in which response performance when detecting the gas components of the gas to be measured may be deteriorated.

That is, the gas to be measured discharged from the discharge opening of the inner hollow-cylindrical portion is circulated in an air space between the side wall of the inner hollow-cylindrical portion and the side wall of the outer hollow-cylindrical portion, and again carried to the inside of the inner hollow-cylindrical portion from the inlet openings of the inner hollow-cylindrical portion. Thereby, the gas to be measured inside the protector may not be sufficiently replaced.

Furthermore, in the gas sensor disclosed in the aforementioned Publication, a reduced diameter portion is formed at the front end of the side wall of the inner hollow-cylindrical portion. A diameter of the reduced diameter portion becomes smaller toward the front end in an axial direction of the inner hollow-cylindrical portion. Also, inlet openings of the outer hollow-cylindrical portion are formed at positions opposite to the reduced diameter portion. Accordingly, the gas to be measured introduced from the inlet openings of the outer hollow-cylindrical portion produces a swirling flow, but sometimes moves in a direction away from the inlet openings of the inner hollow-cylindrical portion along an outer circumferential face of the reduced diameter portion. There are cases in which gas response performance sufficient for detecting the specific gas components cannot be obtained.

The present invention is made to solve the above problems. One object of the present invention is to provide a gas sensor that has excellent response speed and detection accuracy. The gas sensor comprises a protector that covers a gas contact part of a gas sensing element. The protector effectively removes water droplets in a gas to be measured. Also, the protector allows favorable replacement of the gas to be measured. Cases do not occur in which a part of the gas to be measured flown from the inlet openings of the outer hollow-cylindrical portion does not enter the inside of the inner hollow-cylindrical portion, and in which the gas to be measured introduced to the inner part of the inner hollow-cylindrical portion is again carried to the inside of the protector.

To attain the above object, the invention set forth in claim 1 provides a gas sensor comprising a gas sensing element extending in an axial direction and having a gas contact part, which is brought into contact with a gas to be measured, at its front end. The gas sensor also comprises a case that surrounds the gas sensing element in a radial direction in such a manner that the gas contact part protrudes from a front end of the case, and a protector, formed into a bottomed cylinder, fixed to the case in such a manner that the protector covers the gas contact part of the gas sensing element. The protector is composed of an inner hollow-cylindrical portion, and an outer hollow-cylindrical portion which is provided coaxially with a side wall of the inner hollow-cylindrical portion with an air space in between. A bottom wall positioned at an utmost front end of the protector is formed by one of the inner hollow-cylindrical portion and the outer hollow-cylindrical portion. In a side wall of the outer hollow-cylindrical portion, plural number of outer-wall gas inlet openings are formed with guiding bodies extending inward so that the gas to be measured is introduced to the air space. In the side wall of the inner hollow-cylindrical portion, plural number of inner-wall gas inlet openings are formed which are arranged nearer to the case than the outer-wall gas inlet openings so that the gas to be measured is introduced around the gas contact part. An outer circumferential face of the side wall of the inner hollow-cylindrical portion positioned opposite to the outer-wall gas inlet openings is formed so as to be parallel to an outer circumferential face of the side wall of the outer hollow-cylindrical portion or so as to have a slope-like shape with a diameter enlarging in an axial direction toward the bottom wall of the protector. A discharge opening for discharging the gas to be measured, which is introduced to inside of the inner hollow-cylindrical portion directly to outside of the protector, is formed in the bottom wall of the protector.

According to the gas sensor set forth in claim 1, the plural number of outer-wall gas inlet openings with the guiding bodies extending inward are formed in the side wall of the outer hollow-cylindrical portion. These guiding bodies have a function of producing a swirling flow by the gas to be measured which surrounds the outer circumferential face of the inner hollow-cylindrical portion. Due to the inertial force produced with the swirling flow, relatively heavier water droplets and relatively lighter gas components are separated from each other. The separated water droplets are pressed against an inner circumferential face of the outer hollow-cylindrical portion. Thereby, even if water droplets are contained in the gas to be measured, it is difficult for the water droplets to enter the inside of the inner hollow-cylindrical portion. Thus, a function for protecting the gas sensing element is improved. The outer circumferential face of the side wall of the inner hollow-cylindrical portion opposite to the outer-wall gas inlet openings is formed so as to be parallel to the outer circumferential face of the side wall of the outer hollow-cylindrical portion or so as to have a slope-like shape with a diameter enlarging in the axial direction toward the bottom wall of the protector. Moreover, the guiding bodies are formed at the respective outer-wall gas inlet openings so as to be positioned in the air space between the side wall of the inner hollow-cylindrical portion and the side wall of the outer hollow-cylindrical portion. Therefore, the gas to be measured from which moisture is removed and whose specific gravity is lightened can be promptly carried toward the inner-wall gas inlet openings of the inner hollow-cylindrical portion and introduced into the inner hollow-cylindrical portion.

That is, the gas to be measured introduced from the outer-wall gas inlet openings flows toward the inner-wall gas inlet openings along the outer circumferential face of the side wall of the inner hollow-cylindrical portion positioned opposite to the outer-wall gas inlet openings, and further flows surrounding the outer circumference of the inner hollow-cylindrical portion. The gas to be measured hardly flows out to outside of the outer-wall gas inlet openings due to presence of the respective guiding bodies. Thus, the gas to be measured is made to flow toward the inner-wall gas inlet openings.

Accordingly, with the gas sensor of the present invention, a protection function of the gas sensing element by the protector itself against water droplets is improved. Also, replacement of the gas to be measured is promptly performed inside the protector. Thus, it is possible to improve response speed and detection accuracy when detecting the gas components in the gas to be measured.

The invention set forth in FIG. 1 is characterized in that the inner hollow-cylindrical portion is formed into a bottomed cylinder, and the outer hollow-cylindrical portion is formed into a bottomed cylinder. The inner hollow-cylindrical portion is passed through an insertion hole provided in a bottom wall of the outer hollow-cylindrical portion, so that the bottom wall of the inner hollow-cylindrical portion protrudes nearer to the front end than the bottom wall of the outer hollow-cylindrical portion. The bottom wall of this inner hollow-cylindrical portion is made a bottom wall positioned at an utmost front end of the protector, in which the discharge opening is formed.

According to the gas sensor set forth in FIG. 1, the inner hollow-cylindrical portion is provided with the bottom wall having the discharge opening. This bottom wall of the inner hollow-cylindrical portion is formed so as to protrude at the front end from the bottom wall of the outer hollow-cylindrical portion. Therefore, the gas to be measured introduced from the outer-wall gas inlet openings, and the gas to be measured from which the gas components are detected and which is discharged from the discharge opening, are not mixed inside the protector. Favorable replacement of the gas to be measured is achieved inside the protector. Improvement is achieved in the response speed and detection accuracy when detecting the gas components in the gas to be measured.

That is, according to the gas sensor of the present invention, it is possible to prevent the gas to be measured, from which the gas components are detected in the inner hollow-cylindrical portion of the protector and which is directed toward the discharge opening, from being introduced again to the inside of the outer hollow-cylindrical portion of the protector.

It is preferable that an opening area of the discharge opening is in a range from one fiftieth to a half of an area of the bottom wall. The reason is because if the opening area of the discharge opening exceeds a half of the area of the bottom wall, water enters through the discharge opening from the outside of the gas sensor, and easily adheres to the gas sensing element. On the other hand, if the opening area of the discharge opening is smaller than one fiftieth of the area of the bottom wall, discharge performance of the gas to be measured, from which the gas components are detected in the inner hollow-cylindrical portion and which is directed toward the discharge opening, is deteriorated. Hence, the response speed and the detection accuracy when detecting the gas components in the gas to be measured are deteriorated.

The invention set forth in claim 2 is characterized in that, in the gas sensor set forth in claim 2, the side wall of the inner hollow-cylindrical portion, which protrudes nearer to the front end than the bottom wall of the outer hollow-cylindrical portion, has a taper part so that an outer diameter of the side wall becomes smaller toward the front end.

According to the gas sensor set forth in claim 2, the side wall of the inner hollow-cylindrical portion, which protrudes nearer to the front end than the bottom wall of the outer hollow-cylindrical portion, has a taper part so that the outer diameter of the side wall becomes smaller toward the bottom wall of the protector. As a result, the gas to be measured flowing around the outer circumference of a protruding side wall part runs into this taper part so as to produce a gas stream flowing along the taper part. In the present gas sensor, due to the produced gas stream, a negative pressure is generated in a vicinity of the bottom wall positioned at the utmost front end of the protector. Accordingly, the gas to be measured is promptly discharged from the discharge opening formed on this bottom wall. Replacement of the gas to be measured is favorable inside the protector. The response speed and detection accuracy when detecting the gas components in the gas to be measured can be effectively improved.

The invention set forth in FIG. 11A is characterized in that, the bottom wall of the outer hollow-cylindrical portion has a taper part so that that an outer diameter of the bottom wall becomes smaller toward the front end.

According to the gas sensor set forth in FIG. 11A, the bottom wall of the outer hollow-cylindrical portion has a taper part so that the outer diameter of the bottom wall becomes smaller toward the front end. Therefore, in combination with the effect of the taper part in the side wall of the inner hollow-cylindrical portion which protrudes nearer to the front end than the bottom wall of the outer hollow-cylindrical portion, the gas stream flowing along the both taper parts is more smoothly produced. Thereby, replacement of the gas to be measured inside the protector is all the more favorably achieved. The response speed and detection accuracy when detecting the gas components in the gas to be measured can be further improved.

In the gas sensor set forth in FIG. 11A, the inventors of the present invention confirmed that, if a protruding length of the inner hollow-cylindrical portion which protrudes from the bottom wall of the outer hollow-cylindrical portion and has the taper part is in a range from 1 mm to 5 mm, the response speed and detection accuracy when detecting the gas components in the gas to be measured can be improved.

Also, in the gas sensor set forth in FIG. 11A, it is preferable that an angle of the taper part of the inner hollow-cylindrical portion is in a range of $30°≦β≦60°$, where $β$ is an exterior angle at an intersection between the bottom wall of the inner hollow-cylindrical portion and the taper part. By setting the exterior angle in the above range, the gas stream flowing along the taper part can be smoothly produced. Furthermore, by arranging a sensor axis of the gas sensor with an inclination to an exhaust tube, even if a positional relation between the sensor axis and a flowing direction of the gas to be measured differs, the gas to be measured inside the protector can be favorably replaced by setting the $β$ in the above range. The response speed and detection accuracy of the gas sensor can be favorably obtained, regardless of the attachment direction and attachment angle of the gas sensor.

The invention set forth in FIG. 5B is characterized in that the outer hollow-cylindrical portion is formed into a bottomed cylinder. A bottom wall of the outer hollow-cylindrical portion is positioned nearer to the front end than the inner hollow-cylindrical portion, so that the bottom wall of the outer hollow-cylindrical portion is made a bottom wall positioned at an utmost front end. It is preferable that the discharge opening is formed in the bottom wall of the outer hollow-cylindrical portion.

According to the gas sensor set forth in FIG. 5B, the outer hollow-cylindrical portion is provided with the bottom wall having the discharge opening. The bottom wall of this outer hollow-cylindrical portion is positioned nearer to the front end than the inner hollow-cylindrical portion. Therefore, the gas to be measured introduced from the outer-wall gas inlet openings, and the gas to be measured from which the gas components are detected and which is discharged from the discharge opening, are not mixed inside the protector. The favorable replacement of the gas to be measured is achieved. The detection accuracy of the gas components in the gas to be measured and response speed can be improved.

That is, according to the present gas sensor, it is possible to prevent the gas to be measured, from which the gas components are detected in the inner hollow-cylindrical portion of the protector and which is directed toward the discharge opening, from entering again the inside of the outer hollow-cylindrical portion of the protector.

The invention set forth in FIG. 6 is characterized in that the bottom wall of the outer hollow-cylindrical portion is composed of a first bottom wall which is connected to the side wall of the outer hollow-cylindrical portion, and a second bottom wall disposed nearer to the front end than the first bottom wall. The discharge opening is formed in the second bottom wall. A connecting side wall that connects the first bottom wall and the second bottom wall has a taper part so that an outer diameter of the connecting side wall becomes smaller toward the front end.

According to the gas sensor set forth in FIG. 6, the connecting side wall has a taper part so that the outer diameter of the connecting side wall becomes smaller toward the front end. Thus, the gas to be measured flowing around the connecting side wall runs into the taper part so as to produce a gas stream flowing along the taper part. In the present gas sensor, due to the produced gas stream, a negative pressure is generated in a vicinity of the bottom wall (the second bottom wall) positioned at the utmost front end of the protector. Accordingly, the gas to be measured can be promptly discharged from the discharge opening formed on this bottom wall. The gas to be measured can be favorably replaced inside the protector. The detection accuracy and response speed when detecting the gas components in the gas to be measured can be improved.

In the invention set forth in claim 3 is characterized in that, at least one drain hole is formed in a part, in the bottom wall of the outer hollow-cylindrical portion, which is positioned nearer to outside in a radial direction than the outer circumferential face of the side wall of the inner hollow-cylindrical portion.

According to the gas sensor set forth in claim 3, water droplets, contained in the gas to be measured introduced from the outer-wall gas inlet openings, are pressed against the inner circumferential face of the outer hollow-cylindrical portion and condensed due to occurrence of the swirling flow by the guiding bodies. The water droplets can be removed to the outside of the protector via the drain hole. Accordingly, no water droplet is pooled between the respective side walls of the outer hollow-cylindrical portion and the inner hollow-cylindrical portion. Entrance of the water droplets into the inner hollow-cylindrical portion can be more reliably inhibited.

The invention set forth in claim 4 is characterized in that, a drain hole is formed in a region of the side wall of the inner hollow-cylindrical portion which is positioned inside of the outer hollow-cylindrical portion. The drain hole is formed in such a manner that a front side edge, of an inner periphery of the drain hole, which is positioned at the front end in the axial direction of the protector is positioned nearer to the front end in the axial direction of the protector than a rear side edge, of an inner periphery of the outer-wall gas inlet opening positioned at the utmost front end of the side wall of the outer hollow-cylindrical portion, which is positioned at a rear end in the axial direction of the protector.

According to the gas sensor set forth in claim 4, the drain hole is formed in the region of the side wall of the inner hollow-cylindrical portion which is positioned inside of the outer hollow-cylindrical portion. The drain hole is formed in such a manner that the front side edge, of the inner periphery of the drain hole, which is positioned at the front end in the axial direction of the protector, is positioned nearer to the front end in the axial direction of the protector than a rear side edge, of the inner periphery of the outer wall gas inlet positioned at the utmost front end of the side wall of the outer hollow-cylindrical portion, which is positioned at the rear end in the axial direction of the protector. Therefore, the water droplets, contained in the gas to be measured introduced from the outer-wall gas inlet openings, are pressed against the inner circumferential face of the outer hollow-cylindrical portion and condensed due to occurrence of the swirling flow by the guiding bodies. The water droplets can be lead via the drain hole to the discharge opening inside the inner hollow-cylindrical portion and removed to the outside of the protector.

Moreover, according to the gas sensor set forth in claim 4, the drain hole is formed in the side wall of the inner hollow-cylindrical portion. Accordingly, if an axis of the protector (Z in FIG. 7A) is attached with an inclination so as to produce an obtuse angle (as Z1 in FIG. 7A) relative to a flowing direction (a direction Q in FIG. 7) of the gas to be measured flowing around the protector, the gas to be measured flowing around the protector does not flow in from the drain hole. The replacement of the gas to be measured inside the protector can be favorably maintained.

Furthermore, according to the gas sensor set forth in claim 4, the front side edge of the inner periphery of the drain hole is formed so as to be positioned nearer to the front end in the axial direction of the protector than the rear side edge of the inner periphery of the outer-wall gas inlet openings. Therefore, the drain hole does not inhibit a flow of the gas to be measured toward the inner-wall gas inlet openings. The response speed when detecting the gas components in the gas to be measured can be favorably maintained.

In the gas sensor set forth in claim 4, it is preferable that the front side edge of the drain hole is positioned nearer to the front end in the axial direction of the protector than the front side edge of the inner periphery of the outer-wall gas inlet openings, in order to enhance a drainage effect by the drain hole. Also, it is preferable that the front end of the inner periphery of the drain hole formed in the side wall of the inner hollow-cylindrical portion is formed within a distance of 2 mm toward the rear end in the axial direction of the protector, from an inner opening edge of the insertion hole in the bottom wall of the outer hollow-cylindrical portion, in order to achieve favorable drainage.

The invention set forth in claim 5 is characterized in that, further comprises a second guiding body, one end of which is connected to the rear side edge of the inner periphery of the drain hole and the other end of which extends with an inclination so as to come close to a center, in a radial direction, of the protector from the rear side edge of the drain hole toward the front end of the protector.

According to the gas sensor set forth in claim 5, the second guiding body is provided, one end of which is connected to the rear side edge of the inner periphery of the drain hole and the other end of which extends with an inclination so as to come close to the center, in the radial direction, of the protector toward the front end of the protector from the rear side edge of the drain hole. Therefore, water carried into the inner hollow-cylindrical portion from the drain hole can be restrained from flowing toward the gas sensing element. Water adhesion to the gas sensing element can be inhibited.

The invention set forth in claim 6 is characterized in that, a notch that crosses to the axis of the protector is provided in a part of the side wall of the inner hollow-cylindrical portion. A region at the rear end in the axial direction of the protector from this notch is stuck out inward in the radial direction in a manner continuing to the side wall of the inner hollow-cylindrical portion. Thereby, the second guiding body extending in the axial direction of the protector and the drain hole are formed.

According to the gas sensor set forth in claim 6, the notch is provided on the side wall of the inner hollow-cylindrical portion. The region at the rear end in the axial direction of the protector from the notch protrudes inward in the radial direction in such a manner as to continue to the side wall of the inner hollow-cylindrical portion. Thereby, the second guiding body extending in the axial direction of the protector and the drain hole are formed. Accordingly, water passing the drain hole is effectively led to the discharge opening of the inner hollow-cylindrical portion. Water adhesion to the gas sensing element can be inhibited.

It is preferable that the gas sensor set forth in one of claims 4 to 6, as in the invention set forth in claim 7, plural number of drain holes are provided in the side wall of the inner hollow-cylindrical portion, and a total opening area of the plural number of drain holes is smaller than a total opening area of the plural number of inner-wall gas inlet openings. The reason is because, if the total opening area of the plural number of the drain holes is larger than the total opening area of the plural number of the inner-wall gas inlet openings, the gas to be measured flowing into the inner hollow-cylindrical portion from the plural number of holes is increased. The flow of the gas to be measured toward the plural number of inner-wall gas inlet openings is reduced. The response speed when detecting the gas components in the gas to be measured may be possibly damaged.

It is preferable that, in the gas sensor set forth in one of claims 1 to 7, as in the invention set forth in claim 8, an angle of the guiding bodies extending from end parts of the outer-wall gas inlet openings is formed inward in a range from 35° to 70°, relative to a tangent line of the outer circumference of the outer hollow-cylindrical portion. The reason is because if the angle extending from the end parts of the outer-wall gas inlet openings is smaller than 35°, a gas input itself from the outer-wall gas inlet openings may be reduced. Also, an effect, produced by the guiding bodies, of elevating the gas to be measured to the inner-wall gas inlet openings is reduced. The response speed when detecting the gas components in the gas to be measured may be deteriorated. On the other hand, if the angle of the guiding bodies extending from the end parts of the outer-wall gas inlet openings exceeds 70°, a function for making the gas to be measured swirl is deteriorated. Water droplets and the gas components in the gas to be measured cannot be fully separated. The gas to be measured containing water droplets flows inside the inner hollow-cylindrical portion from the inner-wall gas inlet openings. The function for protecting the gas sensing element from adhesion of water droplets is deteriorated.

It is preferable that the plural number of guiding bodies are evenly arranged around the outer hollow-cylindrical portion, and that six or more number of guiding bodies are provided. The reason is because, if the number of the guiding bodies is less than six, when the positions of the guiding bodies opposite to the gas to be measured flowing around the protector are deviated to a circumferential direction of the protector, the swirling speed of the gas to be measured, entered from the outer-wall gas inlet openings and made swirling around the circumferential face of the inner hollow-cylindrical portion by the guiding bodies, is lowered. The response speed when detecting the gas components in the gas to be measured is deteriorated. The upper limit of the number of the guiding bodies can be set at discretion so as not to deteriorate the rigidity of the outer hollow-cylindrical portion.

BRIEF DESCRIPTION OF THE DRAWINGS

FIGS. 5A to 5C are diagrams showing shapes of respective protectors of the example and the comparative examples, which are used in a response speed comparative test;

BEST MODE FOR CARRYING OUT THE INVENTION

Examples of the present invention will be explained hereafter, by way of the accompanying drawings.

FIRST EXAMPLE

Figure 1:
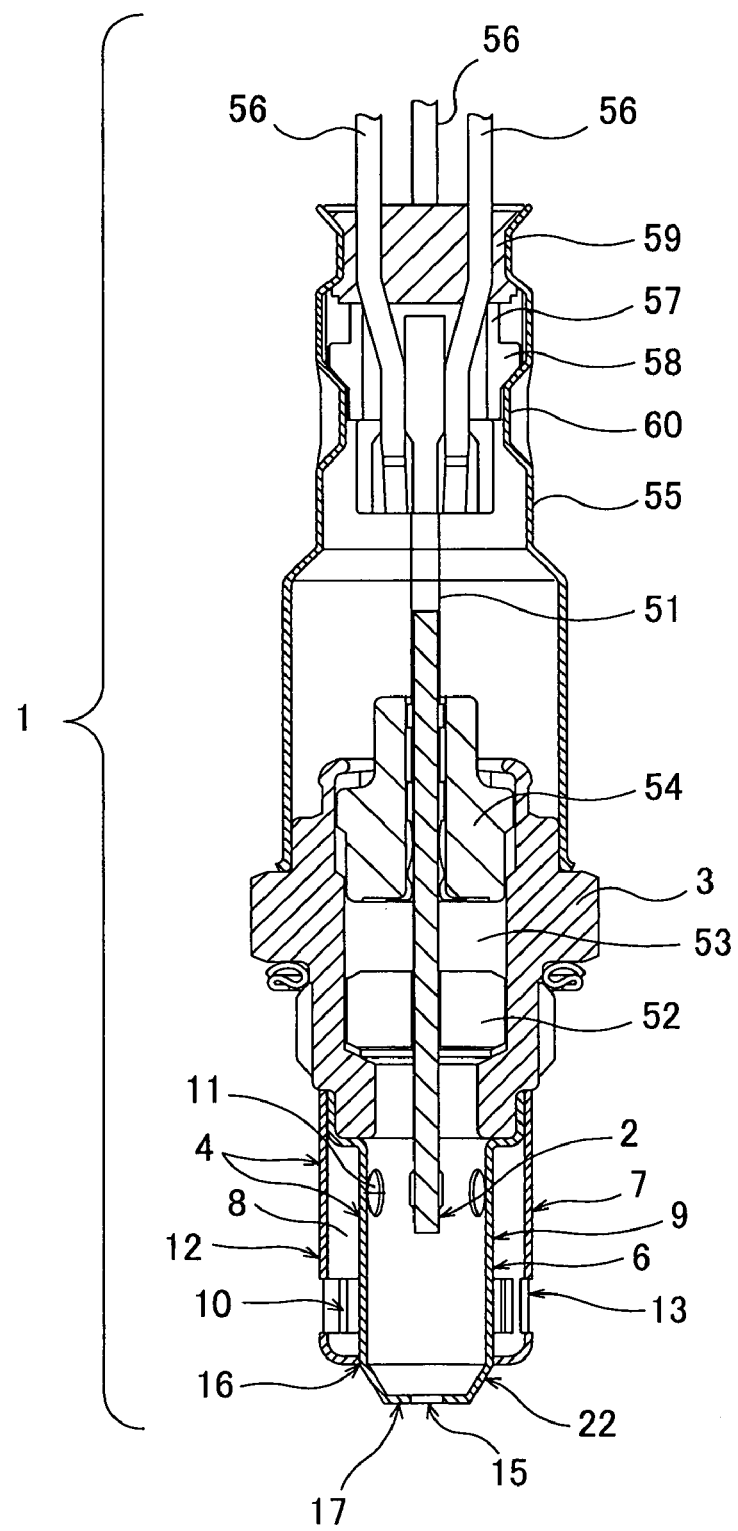
FIG. 1 is a cross sectional view showing a structure of a gas sensor of a first example according to the present invention.
Figure 2:
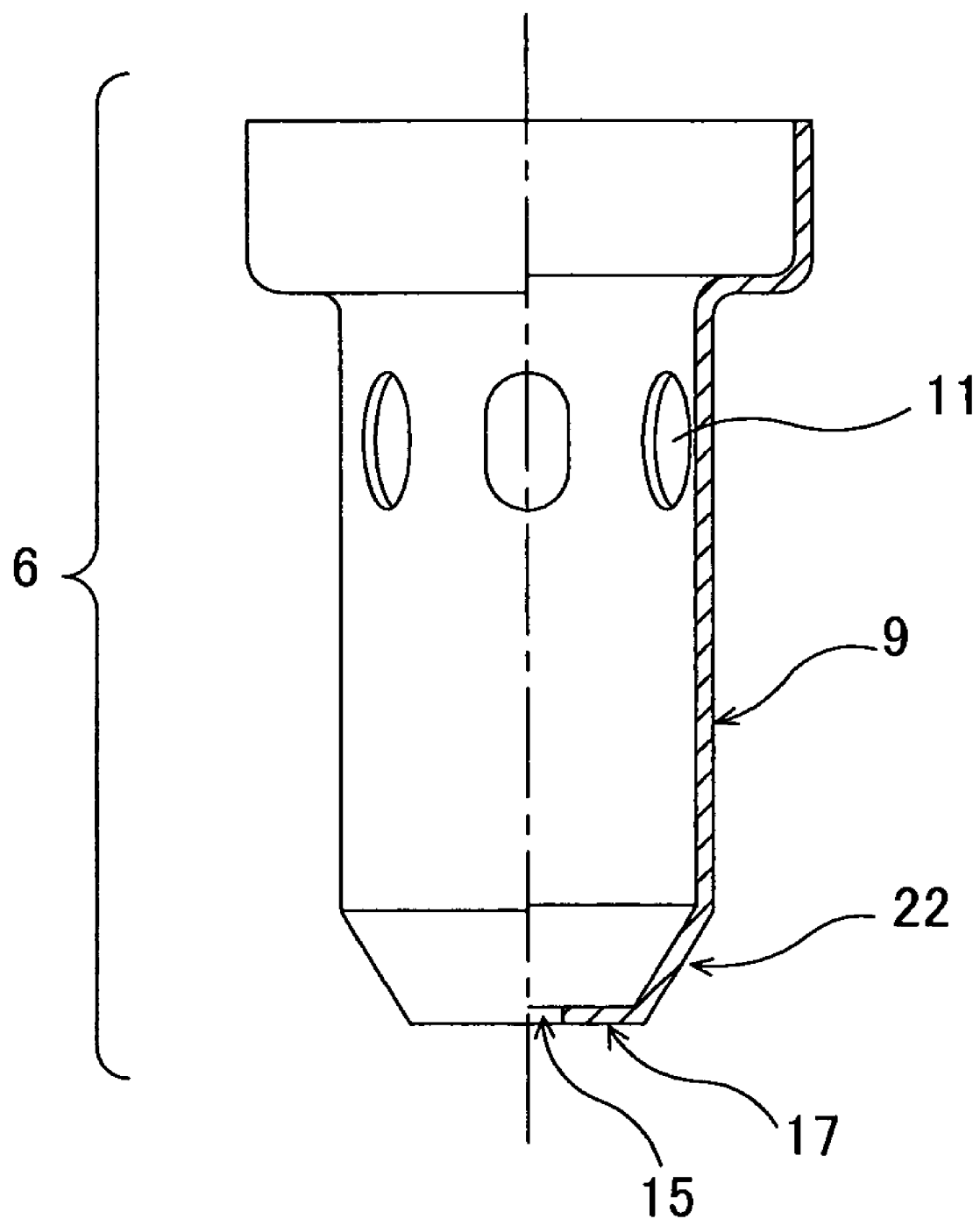
FIG. 2 is a half sectional view showing a shape of an inner hollow-cylindrical portion of the first example.

FIG. 1 is a cross sectional view showing a structure of a gas sensor of a first example according to the present invention according to the present invention. FIG. 2 is a half sectional view showing a shape of an inner hollow-cylindrical portion of the first example. FIG. 3 are, respectively, a half sectional view showing a shape of an outer hollow-cylindrical portion of the first example, and a cross sectional view taken along a line B-B in the foregoing figure.

Referring to FIGS. 1 to 3, a gas sensor 1 comprises a gas sensing element 2 that has a gas contact part, which is brought into contact with a gas to be measured, at a front end (lower side in the figures), a cylindrical case 3 that firmly holds the gas sensing element 2 in such a manner that the gas contact part protrudes from a front end of the case 3, and a bottomed cylindrical protector 4 that is fixed to the outer circumference at the front end of the case 3.

As shown in FIG. 1, the gas sensing element 2 is fixed to the case 3 via a ceramic holder 52, talc powder 53, and a ceramic sleeve 54, in order of disposition from the front end of the case 3. An outer cylinder 55 is fixed to the outer circumference at a rear end of the case 3, by welding, etc. A wire lead 56, which electrically connects the gas sensing element 2 with the outside via a lead frame 51, is passed through a ceramic separator 57 and a grommet 59 both disposed inside at the rear end of the outer cylinder 55. The ceramic separator 57 is provided with a flange part 58, which protrudes outward, on the outer circumferential face at about the middle in an axial direction. The flange part 58 is supported by an outer support portion 60 which protrudes inward in the outer cylinder 55. The grommet 59 is elastically fitted into the outer cylinder 55.

The protector 4 has a two-tiered structure, composed of the inner hollow-cylindrical portion 6, and an outer hollow-cylindrical portion 7 that is coaxially provided outside the inner hollow-cylindrical portion 6 with an air space 8 in between.

Figure 3A:
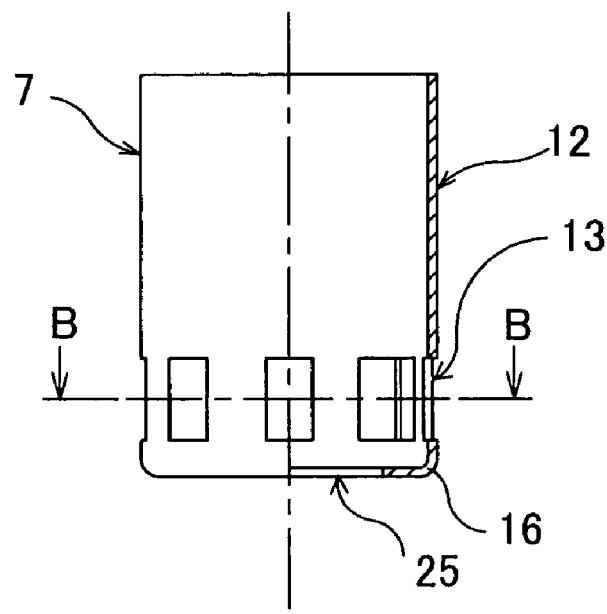
FIG. 3A is a half sectional view showing a shape of an outer hollow-cylindrical portion of the example.
Figure 3B:
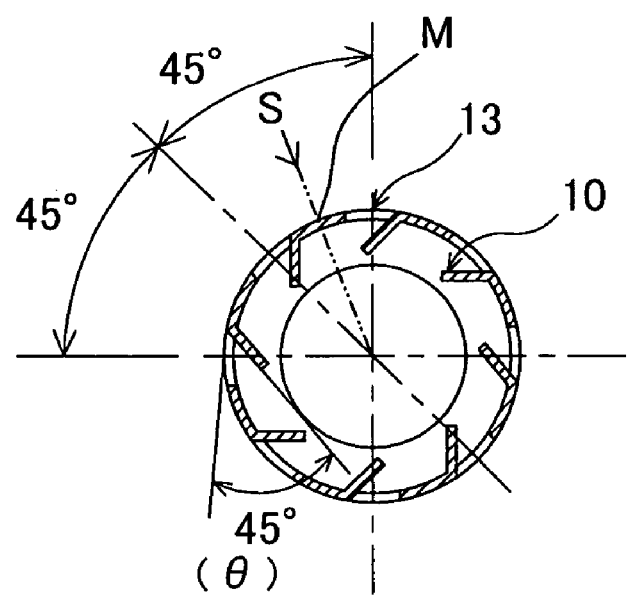
FIG. 3B is a cross sectional view taken along a line B-B in FIG. 3A.

Plural number of (particularly, eight) outer-wall gas inlet openings 13 with guiding bodies 10 extending inward are provided on a side wall 12 of the outer hollow-cylindrical portion 7, at an interval of 45° on the circumference, so as to introduce the gas to be measured into the air space 8 (see FIG. 3B). These guiding bodies 10 are bent inward at an angle of about 45° to a tangent line of the outer circumference of the outer hollow-cylindrical portion 7. As shown in FIGS. 3A and 3B, each of the guiding bodies 10 is formed by cutting the side wall 12 of the outer hollow-cylindrical portion 7 into a U-shape and bending the cut piece. The guiding bodies 10 have a function of producing a swirling flow by the gas to be measured which surrounds the outer circumferential face of the inner hollow-cylindrical portion 6. Due to the inertial force produced with the swirling flow, relatively heavier water droplets and relatively lighter gas components are separated from each other.

On a side wall 9 of the inner hollow-cylindrical portion 6, inner-wall gas inlet openings 11 are formed so as to face the gas sensing element 2, at positions nearer to the case 3 than the outer-wall gas inlet openings 13, so as to introduce the gas to be measured around the gas sensing element 2. The positions of the respective inner-wall gas inlet openings 11 are shifted by 22.5° in a circumferential direction, relative to the outer-wall gas inlet openings 13. The inner-wall gas inlet openings 11 are formed in plural number (particularly, eight) at an interval of 45° on the circumference. The outer circumferential face, of the side wall 9 of the inner hollow-cylindrical portion 6, positioned opposite to the outer-wall gas inlet openings 13 is formed so as to be parallel to the outer circumferential face of the side wall 12 of the outer hollow-cylindrical portion 7.

In the gas sensor 1, the inner hollow-cylindrical portion 6 is formed into a bottomed cylinder, and the outer hollow-cylindrical portion 7 is formed into a bottomed cylinder. The inner hollow-cylindrical portion 6 is passed through an insertion hole 25 (see FIG. 3A) provided in a bottom wall 16 of the outer hollow-cylindrical portion 7. A bottom wall 17 of the inner hollow-cylindrical portion 6 protrudes nearer to the front end than the bottom wall 16 of the outer hollow-cylindrical portion 7. A discharge opening 15 is provided in the bottom wall 17 of the inner hollow-cylindrical portion 6. That is, the bottom wall 17 of the inner hollow-cylindrical portion 6 is made a bottom wall positioned at the utmost front end of the protector 4. An opening area of the discharge opening 15 is set to one fourth of an area of the bottom wall 17.

A taper part 22 is provided in the side wall 9 of the inner hollow-cylindrical portion 6 which protrudes nearer to the front end than the bottom wall 16 of the outer hollow-cylindrical portion 7, so that the diameter of the side wall 9 becomes smaller toward the front end. The exterior angle at which the taper part 22 intersects with the bottom wall 17 is set to 45°.

Hereinafter, an explanation is given, by way of the drawings, on the results of a response speed test in which the gas sensor 1 detects specific gas components in the gas to be measured. For the purpose of confirming the effect of the example of the present invention, comparative tests were conducted with comparative examples.

Figure 4:
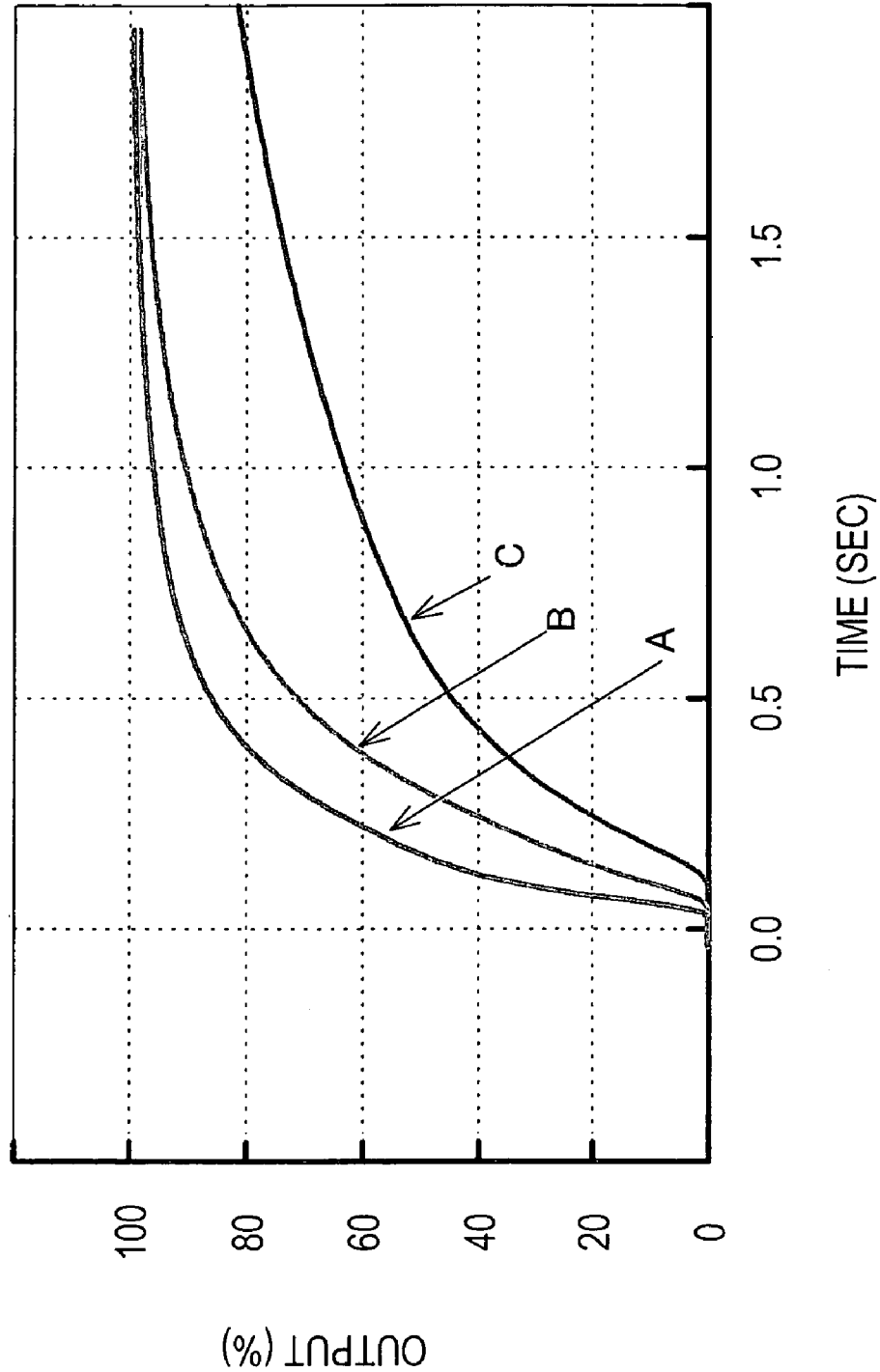
FIG. 4 is a response speed comparative diagram in which response performance is compared between the example and comparative examples.

FIG. 4 is a response speed comparative diagram in which response performance is compared between the example and the comparative examples. FIGS. 5A to 5C are diagrams showing the shapes of protectors according to the present example and the comparative examples used in a response speed comparative test.

Structures of the gas sensors used in the response speed comparative test are briefly explained referring to FIGS. 5A to 5C.

In FIGS. 5A to 5C, FIG. 5A is a cross sectional view of the protector of the first example, FIG. 5B is a cross sectional view of a protector of a first comparative example, and FIG. 5C is a cross sectional view of a protector of a second comparative example.

As shown in FIG. 5A, the protector of the first example has the structure mentioned above. The bottom wall 17 of the inner hollow-cylindrical portion 6 protrudes approximately 3 mm at the front end in an axial direction of the protector 4, from the front end of the side wall 9 of the outer hollow-cylindrical portion 7. The discharge opening 15 is formed in the bottom wall 17. In the side wall of the outer hollow-cylindrical portion 7, the plural number of outer-wall gas inlet openings 13 are formed with the guiding bodies 10 extending inward.

As shown in FIG. 5B, in the protector of the first comparative example, an inner hollow-cylindrical portion 40 is accommodated inside an outer hollow-cylindrical portion 41. Discharge openings 42, 43 are respectively formed on the inner hollow-cylindrical portion 40 and the outer hollow-cylindrical portion 41. A gas to be measured discharged from the discharge opening 42 of the inner hollow-cylindrical portion 40 is firstly discharged to an air space 46 provided between the inner hollow-cylindrical portion 40 and the outer hollow-cylindrical portion 41, and then discharged from the discharge opening 43 of the outer hollow-cylindrical portion 41. In a side wall of the outer hollow-cylindrical portion 41, the plural number of (particularly, eight) outer-wall gas inlet openings 13 are formed with the guiding bodies 10 extending inward (the guiding bodies 10 are bent inward at an angle of 45° to a tangent line of the outer circumference of the outer hollow-cylindrical portion 41). Also, the plural number of (particularly eight) inner-wall gas inlet openings 11 are formed to be positioned nearer to the rear end than the outer-wall gas inlet openings 13. In the first example and the first comparative example, the opening area of the outer-wall gas inlet openings 13 and the opening area of the inner-wall gas inlet openings 11 are set to be substantially the same.

As shown in FIG. 5C, the protector of the second comparative example is formed to have the same structure as the protector of the first comparative example, but without the plural number of guiding bodies 10.

The test was conducted as follows. The gas sensors provided with these protectors were respectively attached so as to protrude into a discharge pipe having an inner diameter of 50 mm. Propane gas was burned using a gas burner and the combustion gas was injected into the discharge pipe at a flow speed of 2.5 m/sec. For the first 0 to 2 seconds from the start of injection by the gas burner, an air excess ratio λ was set to 0.95. After 2 seconds, the air excess ratio was shifted to 1.05.

In FIG. 4, a horizontal axis indicates injection time of the combustion gas by the gas burner. A vertical axis indicates output values when gas components were detected. Herein, an average output value from 0 to 2 seconds is indicated as 0%, and an average output value from 18 to 20 seconds is indicated as 100%. Transitions to the output value of 100% were graphed.

"A" shown in FIG. 4 is a property of the protector of the first example. "B" is a property of the protector of the first comparative example. "C" is a property of the protector of the second comparative example.

The output value of the protector of the first example, shown as the property "A", reached 100% more promptly than the protector of the first comparative example shown as the property "B" and the protector of the second comparative example shown as the property "C". It is found that the protector of the first example is superior in response performance when detecting the gas components in the gas to be measured.

In the protector of the first comparative example, the discharge opening 42 of the inner hollow-cylindrical portion 40 is located inside the outer hollow-cylindrical portion 41. The air space 46 is provided in which the gas to be measured discharged from the discharge opening 42 of the inner hollow-cylindrical portion 40 and the gas to be measured introduced from the outer-wall gas inlet openings 13 of the outer hollow-cylindrical portion 41 are mixed. Accordingly, it is found that the protector of the first comparative example is inferior in response performance for detecting the gas components of the gas to be measured to the protector of the first example.

In the second comparative example, no guiding bodies 10 are attached to the outer-wall gas inlet openings 45 of the outer hollow-cylindrical portion 44. Thus, it is found that the protector of the second comparative example is inferior in response performance when detecting the gas components in the gas to be measured to the protector of the first comparative example.

Figure 9A:
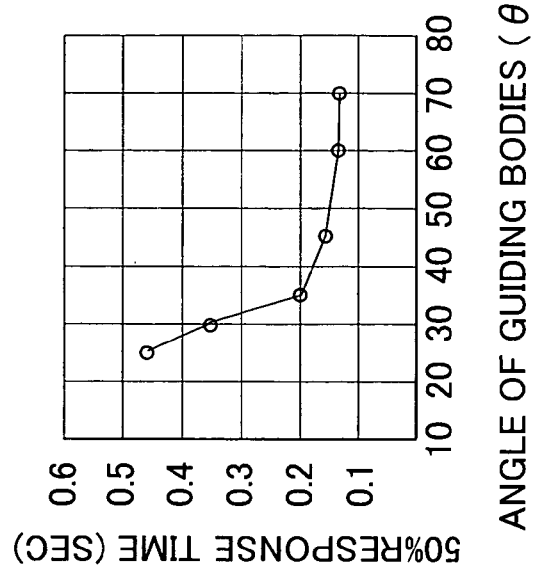
FIG. 9A is a response speed comparative diagram in which, in a response speed test, angles of guiding bodies are varied, and time required for an output value of gas components to reach 50% an output value to reach 50% is measured.

An explanation is given on the results of another response speed test conducted, using the gas sensor of the first example, in the same manner as the aforementioned response speed test. In the present response speed test, the angle (θ in FIG. 3B) of the guiding bodies 10 extending from the outer-wall gas inlet openings 13 is varied from 25° to 70° relative to the tangent line of the outer circumference of the outer hollow-cylindrical portion 7. FIG. 9A is a response speed comparative diagram in which time required for the output value to reach 50% is measured.

As shown in FIG. 9A, if the angle (θ in FIG. 3B) of the guiding bodies 10 extending from the outer-wall gas inlet openings 13 was 35° or above, the time to reach the output value of 50% was not more than 0.2 seconds. Therefore, it is found that the response performance is favorable. On the other hand, if the angle (θ in FIG. 3B) of the guiding bodies 10 extending from the outer-wall gas inlet openings 13 was less than 35°, it is found that the time required to reach the output value of 50% was lengthened.

Figure 10:
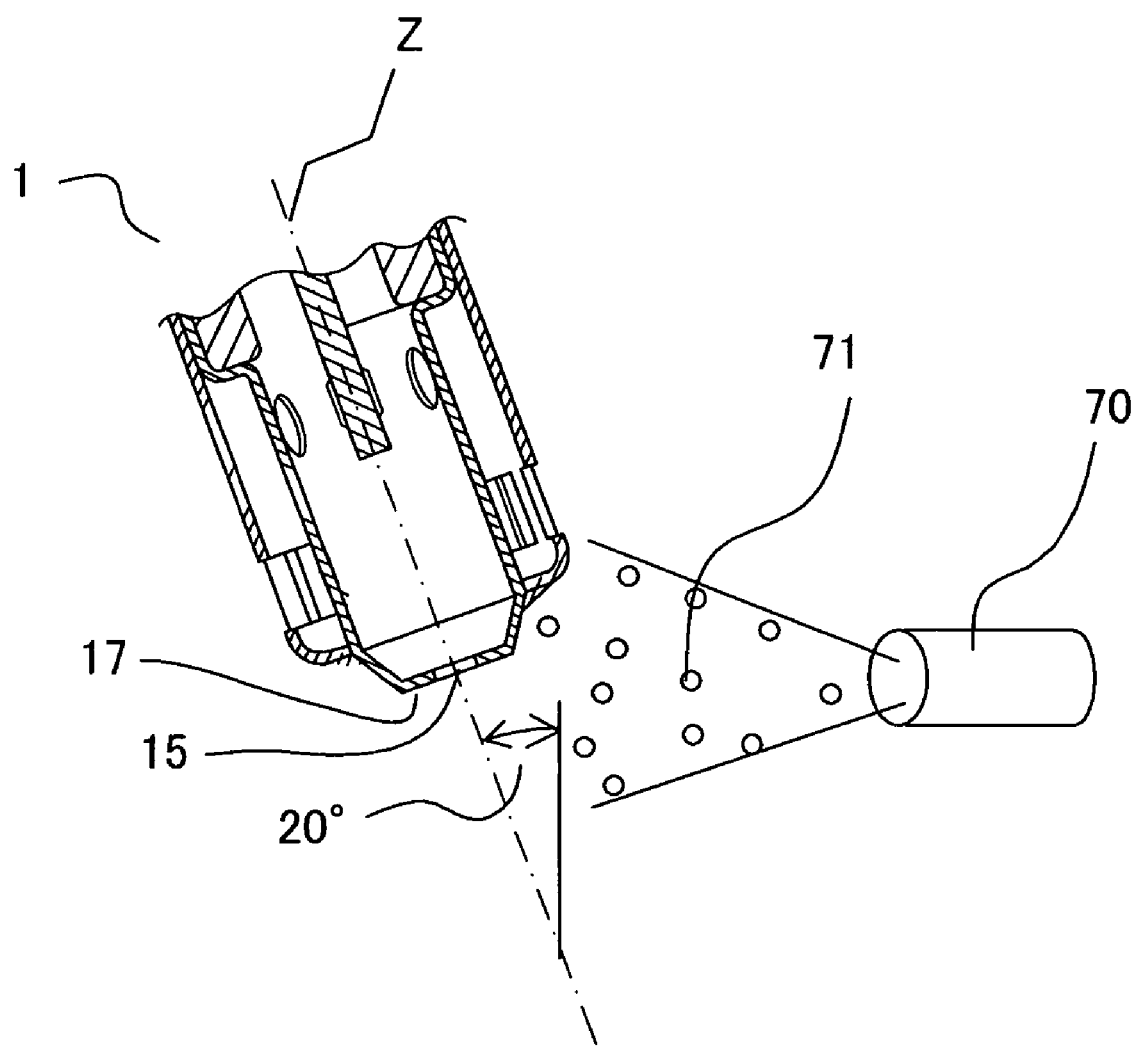
FIG. 10 is a schematic view showing a method for testing water resistance of the gas sensor.

The effect of removing moisture contained in the gas to be measured was confirmed by a water resistance test conducted to the respective protectors of the first example, the first comparative example, and the second comparative example. FIG. 10 is a schematic diagram showing a method for the water resistance test of the gas sensor.

The water resistance test was performed as follows. The gas sensor was set to protrude inside a discharge tube having an inner diameter of 50 mm. Subsequently, as shown in FIG. 10, water droplets 71 were injected toward the gas sensor 1 from a nozzle 70 at an injection pressure of 0.2 MPa inside the discharge tube. Air was blown at a flow rate of 3 m/sec for 5 seconds, and then, stopped for 5 seconds. The above injection, and blowing and stopping of the air, were repeated three times. At this time, water vapor 71 was injected to an axis Z of the gas sensor 1 with an inclination of 20°. Also, as the gas sensor 1 for the test, gas sensors were provided in which, if the area of the bottom wall 17 is set to 1, the opening area of the discharge opening 15 is 0.03, 0.11, 0.26, and 0.51, respectively. Immediately after the water resistance test was conducted, an appearance of the gas sensing element 2 inside the protector was observed to confirm whether there is adhesion of water droplets. As a result, there was no adhesion of water droplets to the gas sensing element 2 in the gas sensors of the first example in which the opening area of the discharge opening 15 is 0.03, 0.11, and 0.26. The sensors were found favorable. On the other hand, adhesion of water droplets to the gas sensing element 2 was observed in the gas sensor of the second example. Accordingly, it is found that attachment of the guiding bodies 10 to the outer-wall gas inlet openings 13 of the protector can remove moisture in the gas to be measured, thus preventing adhesion of water droplets to the gas sensing element 2. Also, slight adhesion of water droplets to the gas sensing element 2 was observed in the sensor of the first example in which the opening area of the discharge opening 15 is 0.51. Accordingly, it is found that, in order to prevent adhesion of water droplets to the gas sensing element 2, it is preferable that the ratio of the area of the bottom wall 17 to the opening area of the discharge opening 15 is one half or below (0.5 or below).

Now, using the gas sensor of the first example, the angle (θ in FIG. 3B) of the guiding bodies 10 extending from the outer-wall gas inlet openings 13 was varied to 35°, 45°, 70°, and 90°. In the same manner as above, the effect of removing moisture contained in the gas to be measured was confirmed by the water resistance test. As a result of the test, when the angle (θ in FIG. 3B) of the guiding bodies 10 is in a range from 35° to 70°, adhesion of water droplets to the gas sensing element 2 was subtle. The sensor was found favorable. On the other hand, when the angle (θ in FIG. 3B) of the guiding bodies 10 is 90°, adhesion of water droplets to the gas sensing element 2 was observed. Accordingly, it is found that, when the angle (θ in FIG. 3B) of the guiding bodies 10 exceeds 70°, the function of the guiding bodies 10 for swirling the gas to be measured is deteriorated, water droplets and the gas components in the gas to be measured cannot be fully separated, the gas to be measured containing water droplets flows into the inner hollow-cylindrical portion 6 from the inner-wall gas inlet openings 11, and thus a function of protecting the gas sensing element 2 from adhesion of water droplets is deteriorated.

SECOND EXAMPLE

Figure 6:
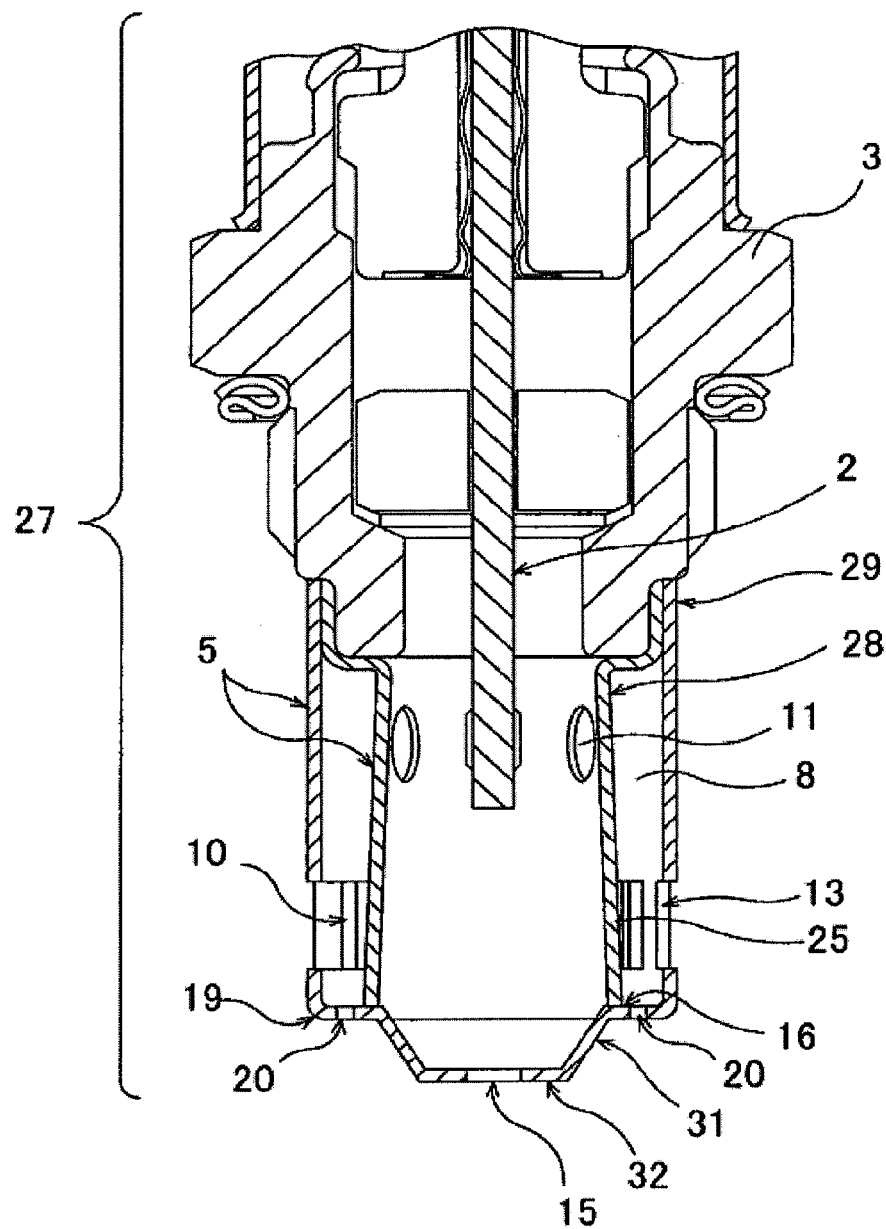
FIG. 6 is a cross sectional view showing a structure of a gas sensor of a second example according to the present invention.

Referring to FIG. 6, the gas sensor of a second example of the present invention is described. The gas sensor in the second example basically has the same structure as the gas sensor described in the first example. Therefore, the same reference numbers are given to the components in common, and detailed descriptions on the same are not repeated. Only the distinguishing parts are explained.

As shown in FIG. 6, a gas sensor 27 comprises a protector 5. The protector 5 has a two-tiered structure composed of an inner hollow-cylindrical portion 28 and a outer hollow-cylindrical portion 29 that is coaxially provided outside the inner hollow-cylindrical portion 28 with an air space 8 in between.

The outer hollow-cylindrical portion 29 has a first bottom wall 19 that is provided nearer to the front end than an end part (front end part) 16 of the inner hollow-cylindrical portion 28, and a second bottom wall 32 that is provided nearer to the front end than the first bottom wall 19. The discharge opening 15 is formed in the second bottom wall 32. A connecting side wall that connects the first bottom wall 19 and the second bottom wall 32 is formed to have a taper part 31 so that a diameter of the connecting side wall becomes smaller toward the front end. That is, the second bottom wall 32 of the outer hollow-cylindrical portion 29 is made a bottom wall positioned at the utmost front end of the protector 5.

The outer circumferential face of a side wall 25 of the inner hollow-cylindrical portion 28 positioned opposite to the outer-wall gas inlet openings 13 is formed so as to have a slope-like shape with a diameter enlarging in an radial direction toward the second bottom wall 32 of the protector 5, in a range from the inner-wall gas inlet openings 11 to the end part 16.

Also, plural number of drain holes 20 are formed in the first bottom wall 19 that is positioned nearer to the outside in an axial direction than the outer circumferential face of the side wall 25 of the inner hollow-cylindrical portion 28. The end part 16 of the inner hollow-cylindrical portion 28 abuts the first bottom wall 19 of the outer hollow-cylindrical portion 29.

THIRD EXAMPLE

Figure 7A:
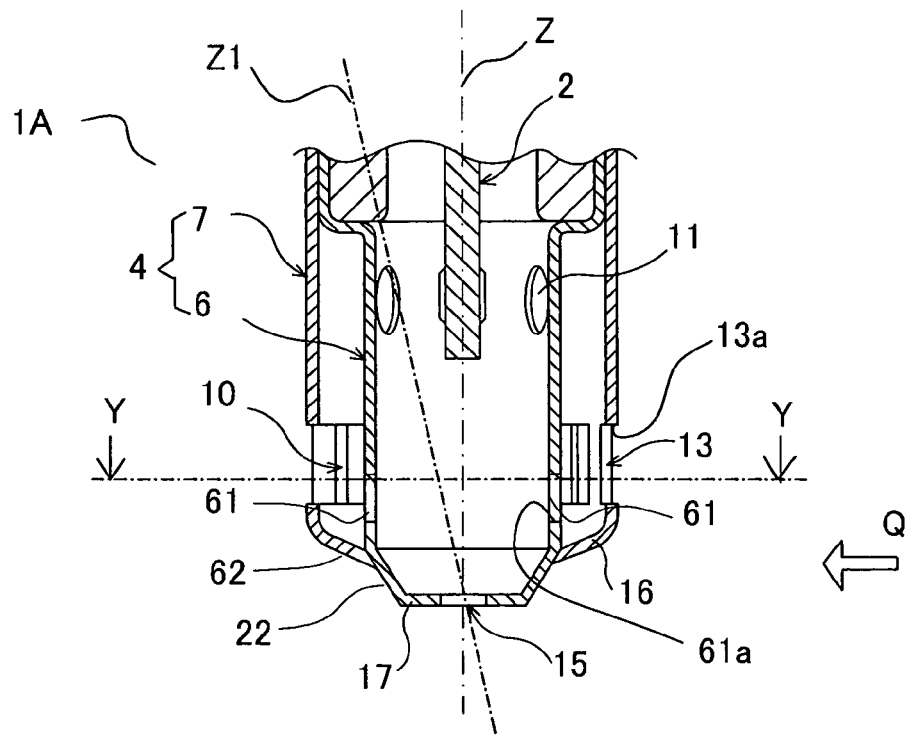
FIG. 7A is a cross sectional view showing a structure of a gas sensor of a third example according to the present invention.
Figure 7B:
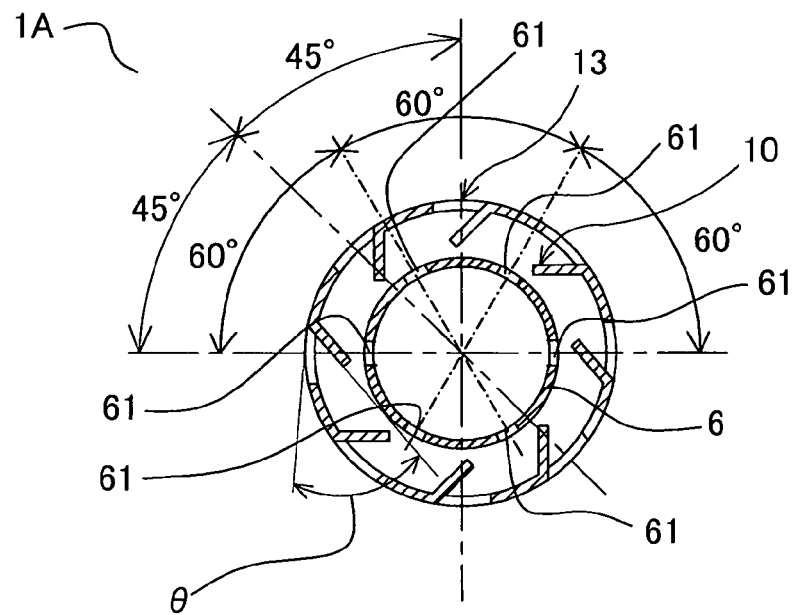
FIG. 7B is a cross sectional view taken along a line Y-Y in FIG. 7A.

Referring to FIGS. 7A and 7B, the gas sensor of a third example of the present invention is described. FIG. 7A is a cross sectional view showing a structure of a gas sensor of the third example according to the present invention. FIG. 7B is a cross sectional view taken along the Y-Y in FIG. 7A. The gas sensor in the third example basically has the same structure as the gas sensor of the first example. Therefore, the same reference numbers are given to the components in common, and detailed descriptions on the same are not repeated. Only the distinguishing parts are explained.

As shown in FIG. 7A, a gas sensor 1A is provided with second drain holes 61 in the side wall of the inner hollow-cylindrical portion 6. In the second drain holes 61, a front side edge 61a of the inner circumferential edge of the second drain holes 61 is formed nearer to the front end side in a direction of axis Z of the protector 4 than the rear side edge 13a of the inner circumferential edge of the outer-wall gas inlet openings 13 (in more details, nearer than the front side edge 13b of the inner circumferential edge of the outer-wall gas inlet openings 13). The front side edge 61a of the drain holes 61 is formed at a distance of 1.5 mm in the direction of axis Z of the protector 4, from the inner (rear end) opening edge of a hole, in the outer hollow-cylindrical portion 7, through which the bottom wall 17 is inserted. The taper part 22 is provided in the side wall of the inner hollow-cylindrical portion 6 protruding nearer to the front end than the bottom wall of the outer hollow-cylindrical portion 7, so that the outer diameter of the side wall becomes smaller toward the bottom end of the protector 4. A taper part 62 is also provided on the bottom wall of the outer hollow-cylindrical portion 7, so that the outer diameter of the bottom wall becomes smaller toward the bottom end of the protector 4.

As shown in FIG. 7B, a total of six second drain holes 61 are provided at an interval of 60° along the circumferential direction of the side wall of the inner hollow-cylindrical portion 6.

Also, the total opening area of the plural number of second drain holes 61 is formed so as to be smaller than the total opening area of the plural number of inner-wall gas inlet openings 11.

Figure 9B:
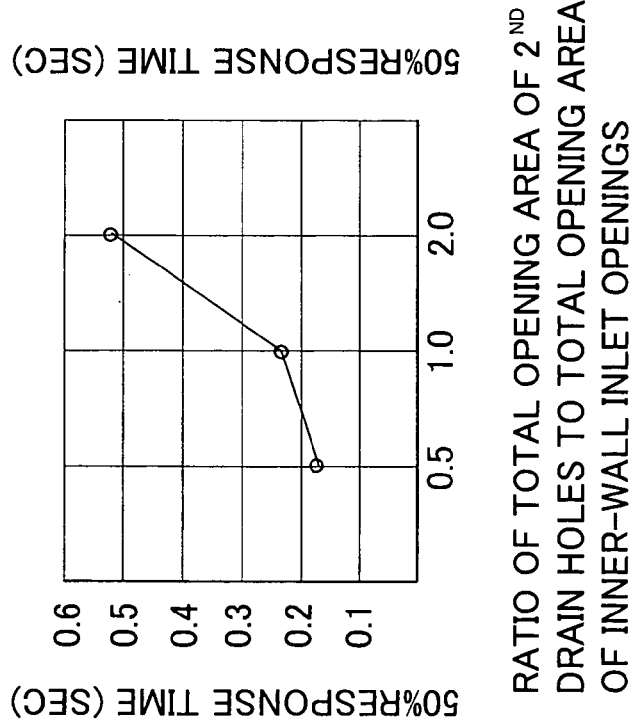
FIG. 9B is a response speed comparative diagram in which, in the response speed test, a total opening area of plural number of second drain holes is varied, and time required for the output value of gas components to reach 50%.

The results of the response speed test, using the gas sensor 1A of the third example, are explained. The test was conducted in the same manner as above. The total opening area of the plural number of second drain holes 61 is varied, and the specific gas elements in the gas to be measured were detected. FIG. 9B is a response speed comparative diagram in which, in the response speed test, the total opening area of the second drain holes 61 is varied, and the time required for the output value to reach 50% is measured. Also, as the gas sensor 1A for the test, gas sensors were provided in which, if the total opening area of the plural number of inner-wall gas inlet openings 11 is set to 1, the opening area of the plural number of second drain holes 61 is 0.5, 1.0, and 2.0, respectively.

As shown in FIG. 9B, if the total opening area of the second drain holes 61 is 0.5 or below, the time required for the output value to reach 50% was not more than 0.2 seconds. A favorable result was obtained. On the other hand, it is found that, if the total opening area of the second drain holes 61 exceeds 0.5, the time required for the output value to reach 50% was lengthened.

FOURTH EXAMPLE

Figure 8A:
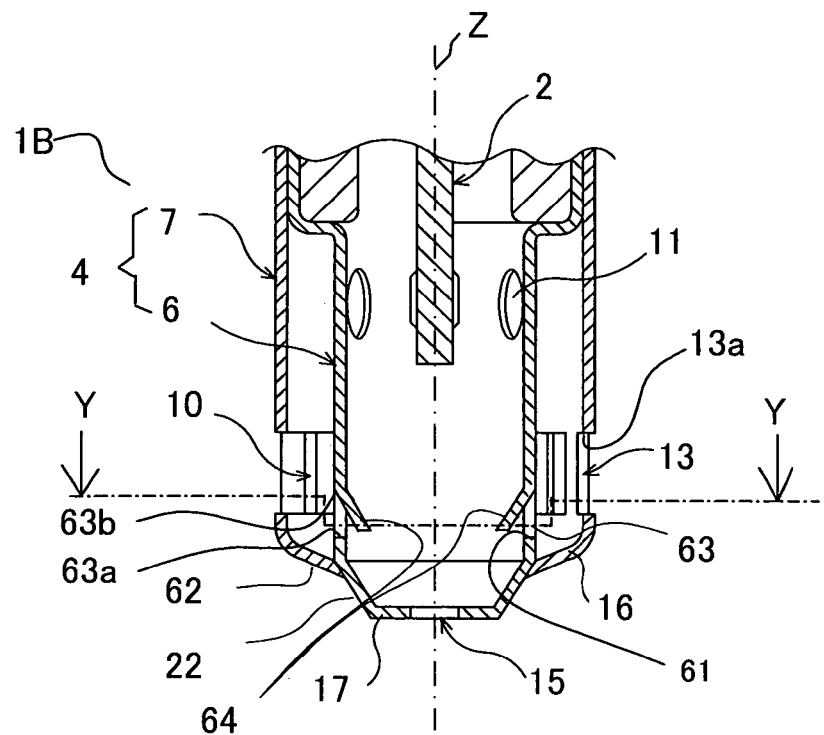
FIG. 8A is a cross sectional view showing a structure of a gas sensor of a fourth example according to the present invention.
Figure 8B:
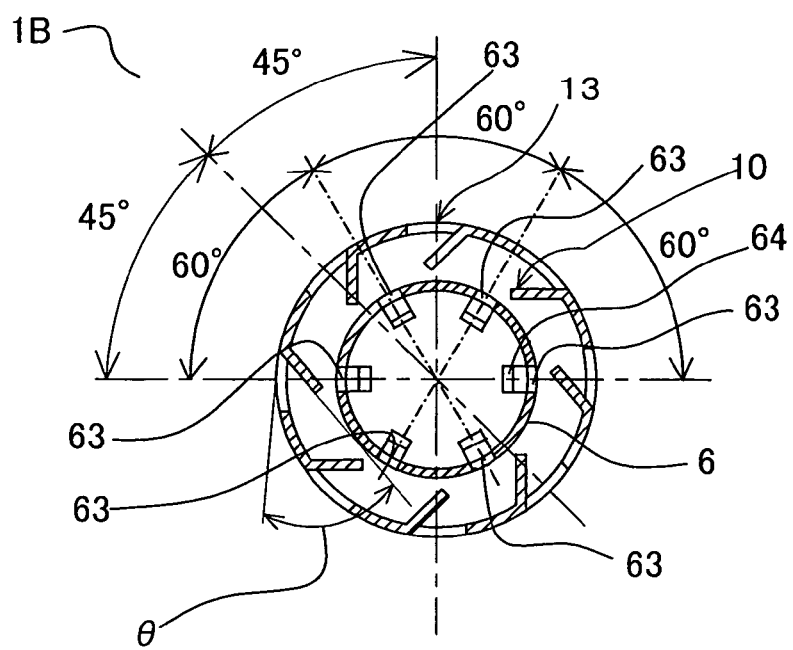
FIG. 8B is a cross sectional view taken along a line Y-Y in FIG. 8A.

Referring to FIGS. 8A and 8B, the gas sensor of a fourth example of the present invention is described. FIG. 8A is a cross sectional view showing a structure of a gas sensor of the fourth example according to the present invention. FIG. 8B is a cross sectional view taken along a line Y-Y in FIG. 8A. The gas sensor in the fourth example basically has the same structure as the gas sensor of the first example. Therefore, the same reference numbers are given to the components in common, and detailed descriptions on the same are not repeated. Only the distinguishing parts are explained.

As shown in FIG. 8A, a gas sensor 1B is provided with second drain holes 63 in the side wall of the inner hollow-cylindrical portion 6. In the second drain holes 63, a front side edge 63a of the inner circumferential edge of the second drain holes 63 is provided nearer to the front end in the direction of axis Z of the protector 4 than the rear side edge 13a of the inner circumferential edge of the outer-wall gas inlet openings 13 (in more details, nearer than the front side edge 13b of the inner circumferential edge of the outer-wall gas inlet openings 13).

The second drain holes 63 are provided with second guiding bodies 64. One ends of the second guiding bodies 64 are connected to a rear side edge 63b of the second drain holes 63. The other ends of the second guiding bodies 64 extend running from the rear side edge 63 of the second drain hole 63 toward the front end of the protector 4 with an inclination, so as to come close to the center, in a radial direction, of the protector 4.

As shown in FIG. 8B, a total of six second drain holes 63 are provided at an interval of 60° along the circumferential direction of the side wall of the inner hollow-cylindrical portion 6.

FIFTH EXAMPLE

Figure 11A:
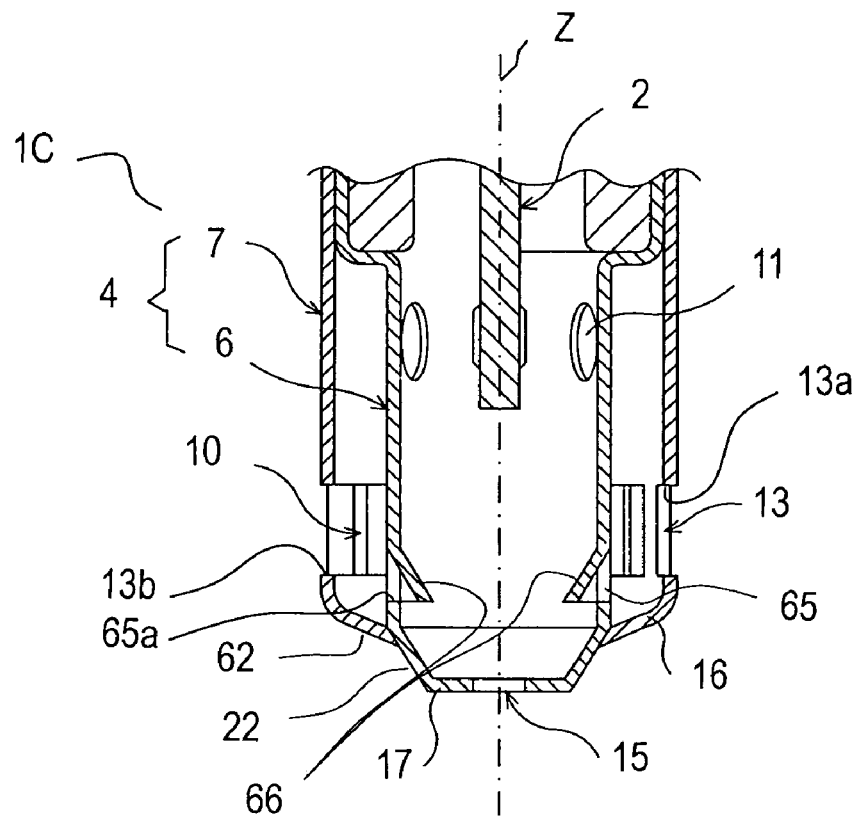
FIG. 11A is a cross sectional view showing a structure of a gas sensor of a fifth example according to the present invention.
Figure 11B:
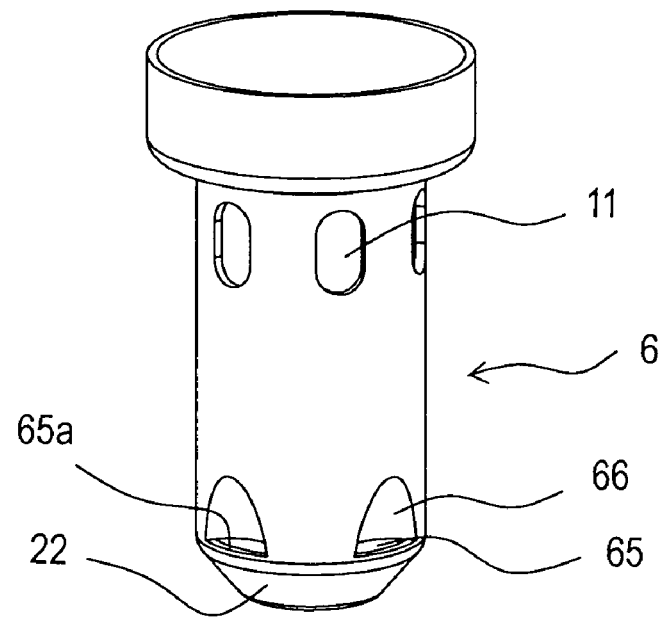
FIG. 11B is a perspective view of an inner hollow-cylindrical portion.

Referring to FIGS. 11A and 11B, the gas sensor of a fifth example of the present invention is described. FIG. 11A is a cross sectional view showing a structure of a gas sensor of the fifth example according to the present invention. FIG. 11B is a perspective view of the inner hollow-cylindrical portion 6. The gas sensor in the fifth example basically has the same structure as the gas sensor of the first example. Therefore, the same reference numbers are given to the components in common, and detailed descriptions on the same are not repeated. Only the distinguishing parts are explained.

As shown in FIG. 11A, a gas sensor 1C is provided with second drain holes 65 in the side wall of the inner hollow-cylindrical portion 6. A front side edge 65a of the inner circumferential edge of the second drain holes 65 is provided nearer to the front end of the protector 4 in the direction of axis Z than the rear side edge 13a of the inner circumferential edge of the outer-wall gas inlet openings 13 (in more details, nearer than the front side edge 13b of the inner circumferential edge of the outer-wall gas inlet openings 13).

In the gas sensor 1C, notches crossing to the direction of axis Z of the protector 4 is provided in parts of the side wall 6 of the inner hollow-cylindrical portion 6 positioned inside the outer hollow-cylindrical portion 7. Regions at the rear end in the direction of axis Z of the protector 4 from the notches are stuck out inward in a radial direction with a curve, in a manner continuing to the side wall of the inner hollow-cylindrical portion 6. As a result, as shown in FIG. 11B, second guiding bodies 66 extending in the direction of axis Z of the protector 4 and the second drain hole 65 are formed. A total of six second drain holes 65 are provided at an interval of 60° along the circumferential direction of the side wall of the inner hollow-cylindrical portion 6.

The effects produced by the use of the gas sensors of the first to fifth examples having the above explained structures are described hereafter.

According to the gas sensors 1, 27, 1A, 1B, 1C of the examples of the present invention, the gas to be measured flows promptly toward the inner-wall gas inlet openings 11 of the inner hollow-cylindrical portions 6, 28. Replacement of the gas to be measured inside the protectors 4, 5 can be enhanced. Response speed and detection accuracy when detecting the gas components in the gas to be measured can be improved.

Also, according to the gas sensors 1, 27, 1A, 1B, 1C of the examples of the present invention, the gas to be measured introduced from the outer-wall gas inlet openings 13 and the gas to be measured directed toward the discharge opening 15 from the inside of the inner hollow-cylindrical portions 6, 28 are not mixed inside the protectors 4, 5. The replacement of the gas to be measured can be enhanced. The response speed and detection accuracy when detecting the gas components in the gas to be measured can be improved.

According to the gas sensor 27 of the second example, moisture, carried from the outer-wall gas inlet openings 13 with the gas to be measured and condensed inside the air space 8 between the inner hollow-cylindrical portion 28 and the outer hollow-cylindrical portion 29, can be removed to the outside of the protector 5 via the drain holes 20 of the first bottom wall 19. Therefore, adhesion of water droplets to the gas sensing element 2 can be reliably avoided.

According to the gas sensors 1, 27, 1A, 1B, 1C of the examples of the present invention, the angle θ of the guiding bodies 10 extending from the ends of the outer-wall gas inlet openings 13 is set inward in a range from 35° to 70° relative to the tangent line of the outer circumference of the outer hollow-cylindrical portions 7, 29. Therefore, the gas to be measured can be led promptly to the inner-wall gas inlet openings 11 of the inner hollow-cylindrical portions 6, 28. Excellent response speed can be maintained. The gas sensing element 2 can be protected from adhesion of water droplets.

According to the gas sensors 1A, 1B, 1C of the third to fifth examples, the second drain holes 61, 63, 65 are formed in the side wall of the inner hollow-cylindrical portion 6. The second drain holes 61, 63, 65 are formed in such a manner that the front side edges 61a, 63a, 65a of the second drain holes 61, 63, 65 are at positions nearer to the front end in the direction of the axis Z of the protector 4 than the rear side edge 13a of the inner circumferential edge of the outer-wall gas inlet openings 13. Therefore, water droplets, in the gas to be measured introduced from the outer-wall gas inlet openings 13, pressed onto the inner circumferential face of the outer hollow-cylindrical portion 7 and condensed due to occurrence of the swirling flow by the guiding bodies can be led into the inner hollow-cylindrical portion 6 via the second drain holes 61a, 63a, 65a, and discharged to the outside of the protector 4 via the discharge opening 15.

According to the gas sensors 1A, 1B, 1C of the third to fifth examples, the second drain holes 61, 63, 65 are formed in the side wall of the inner hollow-cylindrical portion 6. Therefore, if the protector 4 is attached in such a manner that the axis Z of the protector 4 is inclined so as to produce an obtuse angle (like Z1 in FIG. 7A) against the flowing direction (a direction Q in FIG. 7A) of the gas to be measured around the protector 4, the gas to be measured does not easily flow in from the second drain holes 61, 63, 65. Favorable replacement of the gas to be measured can be maintained inside the protector 4.

The present invention is not limited to the above examples, and other modifications and variations may be possible.

For instance, the discharge opening 15 was formed into a hole having the thickness of the bottom walls 17, 32 of the protectors 4, 5. However, this opening can be formed so as to protrude outward by burring, etc.

In the gas sensor 27 of the second example, the side wall 25 of the inner hollow-cylindrical portion 28 opposite to the outer-wall gas inlet openings 13 is formed with an inclination starting from the inner-wall gas inlet openings 11 and ending to the end part 16. However, only parts of the outer circumferential face opposite to the outer-wall gas inlet openings 13 may be formed with an inclination.

The side wall 9 of the inner hollow-cylindrical portion 6 can be inserted so as to make close contact with the end surface of the insertion hole 25 of the outer hollow-cylindrical portion 7. Or, a slight gap may be formed which does not, in effect, allow flowing of the gas to be measured into the outer hollow-cylindrical portion 7.

The end part 16 of the side wall 25 of the inner hollow-cylindrical portion 28 may make close contact with the first bottom wall 19 of the outer hollow-cylindrical portion 29. Or, a slight gap may be formed for drainage of water.

The invention claimed is:

1. A gas sensor comprising:
a gas sensing element extending in an axial direction, and having a gas contact part, which is brought into contact with a gas to be measured, at its front end;
a case that surrounds the gas sensing element in a radial direction in such a manner that the gas contact part protrudes from a front end of the case; and
a protector, formed into a bottomed cylinder, fixed to the case in such a manner that the protector covers the gas contact part of the gas sensing element, wherein
the protector is composed of an inner hollow-cylindrical portion, and an outer hollow-cylindrical portion which is provided coaxially with a side wall of the inner hollow-cylindrical portion with an air space in between,
the inner hollow-cylindrical portion is formed into a bottomed cylinder, the outer hollow-cylindrical portion is formed into a bottomed cylinder, the inner hollow-cylindrical portion is passed through an insertion hole provided in a bottom wall of the outer hollow-cylindrical portion, so that the bottom wall of the inner hollow-cylindrical portion protrudes nearer to the front end than the bottom wall of the outer hollow-cylindrical portion, the bottom wall of this inner hollow-cylindrical portion being made a bottom wall positioned at an utmost front end of the protector,
plural number of outer-wall gas inlet openings are formed in a side wall of the outer hollow-cylindrical portion, with guiding bodies extending inward so that the gas to be measured is introduced to the air space,
plural number of inner-wall gas inlet openings are formed in the side wall of the inner hollow-cylindrical portion, the inner-wall gas inlet openings being arranged nearer to the case than the outer-wall gas inlet openings so that the gas to be measured is introduced around the gas contact part, and, an outer circumferential face of the side wall of the inner hollow-cylindrical portion positioned opposite to the outer-wall gas inlet openings is formed so as to be parallel to an outer circumferential face of the side wall of the outer hollow-cylindrical portion or so as to have a slope-like shape with a diameter enlarging in an axial direction toward the bottom wall of the protector, and
a discharge opening for discharging the gas to be measured, which is introduced to inside of the inner hollow-cylindrical portion directly to outside of the protector, is formed in the bottom wall positioned at the utmost front end of the protector,
wherein the side wall of the inner hollow-cylindrical portion, which protrudes nearer to the front end than the bottom wall of the outer hollow-cylindrical portion, has a taper part so that an outer diameter of the side wall becomes smaller toward the front end, and the bottom wall of the outer hollow-cylindrical portion has a taper part so that that an outer diameter of the bottom wall becomes smaller toward the front end, and
wherein a tip end of the taper part of the bottom wall of the outer hollow-cylindrical portion faces the taper part of the side wall of the inner hollow-cylindrical portion.

2. The gas sensor set forth in claim 1, wherein the side wall of the inner hollow-cylindrical portion, which protrudes nearer to the front end than the bottom wall of the outer hollow-cylindrical portion, has a taper part so that an outer diameter of the side wall becomes smaller toward the front end, and a protruding length of the inner hollow-cylindrical portion which protrudes from the bottom wall of the outer hollow-cylindrical portion and has the taper part is in a range from 1 mm to 5 mm.

3. The gas sensor set forth in claim 1, wherein at least one drain hole is formed in a part, in the bottom wall of the outer hollow-cylindrical portion, which is positioned nearer to outside in a radial direction than the outer circumferential face of the side wall of the inner hollow-cylindrical portion.

4. The gas sensor set forth in claim 1, wherein
a drain hole is formed in a region of the side wall of the inner hollow-cylindrical portion which is positioned inside of the outer hollow-cylindrical portion, and
the drain hole is formed in such a manner that a front side edge, of an inner periphery of the drain hole, which is positioned at the front end in the axial direction of the protector is positioned nearer to the front end in the axial direction of the protector than a rear side edge, of an inner periphery of the outer-wall gas inlet opening positioned at an utmost front end of the side wall of the outer hollow-cylindrical portion, which is positioned at a rear end in the axial direction of the protector.

5. The gas sensor set forth in claim 4, further comprising a second guiding body, one end of which is connected to the rear side edge of the inner periphery of the drain hole and the other end of which extends with an inclination so as to come close to a center, in a radial direction, of the protector from the rear side edge of the drain hole toward the front end of the protector.

6. The gas sensor set forth in claim 4, wherein a notch crossing to the axis of the protector is provided in a part of the side wall of the inner hollow-cylindrical portion, and a region at the rear end in the axial direction of the protector from this notch is stuck out inward in the radial direction in such a manner as to continue to the side wall of the inner hollow-cylindrical portion, thereby, forming the second guiding body extending in the axial direction of the protector and the drain hole.

7. The gas sensor set forth in claim 4, wherein plural number of drain holes are provided in the side wall of the inner hollow-cylindrical portion, and a total opening area of the plural number of drain holes is smaller than a total opening area of the plural number of inner-wall gas inlet openings.

8. The gas sensor set forth in claim 1, wherein an angle of the guiding bodies extending from end parts of the outer-wall gas inlet openings is formed inward in a range from 35° to 70° , relative to a tangent line of an outer circumference of the outer hollow-cylindrical portion.

9. A gas sensor comprising:

a gas sensing element extending in an axial direction, and having a gas contact part, which is brought into contact with a gas to be measured, at its front end;

a case that surrounds the gas sensing element in a radial direction in such a manner that the gas contact part protrudes from a front end of the case; and a protector, formed into a bottomed cylinder, fixed to the case in such a manner that the protector covers the gas contact part of the gas sensing element, wherein the protector is composed of an inner hollow-cylindrical portion, and an outer hollow-cylindrical portion which is provided coaxially with a side wall of the inner hollow-cylindrical portion with an air space in between, the outer hollow-cylindrical portion is formed into a bottomed cylinder, and a bottom wall of the outer hollow-cylindrical portion is disposed nearer to the front end than the inner hollow-cylindrical portion, so that the bottom wall of the outer hollow-cylindrical portion is made a bottom wall positioned at an utmost front end of the protector, plural number of outer-wall gas inlet openings are formed in a side wall of the outer hollow-cylindrical portion, with guiding bodies extending inward so that the gas to be measured is introduced to the air space, plural number of inner-wall gas inlet openings are formed in the side wall of the inner hollow-cylindrical portion, the inner-wall gas inlet openings being arranged nearer to the case than the outer-wall gas inlet openings so that the gas to be measured is introduced around the gas contact part, and, an outer circumferential face of the side wall of the inner hollow-cylindrical portion positioned opposite to the outer-wall gas inlet openings is formed so as to be parallel to an outer circumferential face of the side wall of the outer hollow-cylindrical portion or so as to have a slope-like shape with a diameter enlarging in the axial direction toward the bottom wall of the protector, a discharge opening for discharging the gas to be measured, which is introduced to inside of the inner hollow-cylindrical portion directly to outside of the protector, is formed in the bottom wall positioned at the utmost front end of the protector, the bottom wall of the outer hollow-cylindrical portion is composed of a first bottom wall which is connected to the side wall of the outer hollow-cylindrical portion, and a second bottom wall disposed nearer to the front end than the first bottom wall, the discharge opening being formed in the second bottom wall, and a connecting side wall that connects the first bottom wall and the second bottom wall has a taper part so that an outer diameter of the connecting side wall becomes smaller toward the front end.

* * * * *